United States Patent [19]
Crawford et al.

[11] Patent Number: 5,564,345
[45] Date of Patent: Oct. 15, 1996

[54] STACKABLE TABLE, TABLE ASSEMBLY, AND TRAY AND TABLE COMBINATION

[75] Inventors: Edward F. Crawford, Waite Hill; Felix J. Tarorick, Independence; Terry M. Philips, Willoughby, all of Ohio

[73] Assignee: Park Ohio Industries Inc., Cleveland, Ohio

[21] Appl. No.: 60,244

[22] Filed: May 11, 1993

[51] Int. Cl.⁶ ............................................. A47B 7/00
[52] U.S. Cl. ........................................ 108/91; 108/159
[58] Field of Search .................... 108/91, 53.3, 53.5, 108/53.1, 159

[56] References Cited

U.S. PATENT DOCUMENTS

| | | |
|---|---|---|
| D. 215,858 | 11/1969 | Hamilton . |
| D. 217,261 | 4/1970 | Gianfagna . |
| D. 224,494 | 8/1972 | Kerman . |
| D. 240,186 | 6/1976 | Rosen . |
| D. 250,313 | 11/1978 | Miller . |
| D. 346,704 | 5/1994 | Grosfillex . |
| 1,738,429 | 12/1929 | Heyman . |
| 3,688,707 | 9/1972 | White . |
| 3,742,869 | 7/1973 | Polsky et al. . |
| 4,467,730 | 8/1984 | Borichevsky . |
| 4,779,541 | 10/1988 | Milward . |
| 4,841,877 | 6/1989 | Virtue . |

OTHER PUBLICATIONS

"Interiors", Oct. '86, p. 51, Table Top, Top Left, Copy.
Official Gazette Abstract For U.S. Pat. No. 4,974,526 (Dec. 4, 1990).
Official Gazette Abstract For U.S. Pat. No. 4,107,897 (Aug. 22, 1978).
Best Catalog, Spring, 1993, p. 38.
Exhibit A, Stacking Table, Manufacturer Unknown.
Exhibit B, Stacking Table, Syroco.
Exhibit C, Stacking Table, Syroco.
Exhibit D, Left, Stacking Table, Backyard Products, Inc. Erie, PA.
Exhibit D, Right, Stacking Table, Grosfillex, Copyright 1990.
Exhibit E, Table and Tray Combination, Rubbermaid, Wooster, Ohio, "Jan. 1993" Mold Marking.

*Primary Examiner*—Peter M. Cuomo
*Assistant Examiner*—Gerald A. Anderson
*Attorney, Agent, or Firm*—Renner, Otto, Boisselle & Sklar

[57] ABSTRACT

A table that is useful alone and in combination with a tray and/or other inserts supported atop the table. The table is of a unitary molded plastic construction and is configured for nested stacking with like tables for convenient and compact storage and handling. The table has a top surface of regular polygonal shape with four truncated corners, and a plurality of legs depending from the table top at respective ones of the truncated corners. The legs, going from top to bottom, diverge outwardly with each being in the form of a channel that opens inwardly for nested receipt of a corresponding leg of a subjacent table of like construction. The table top has an upstanding marginal rim extending along the peripheral edge of the top surface thereof, and the marginal rim functions to prevent objects from rolling or sliding off the top surface and/or as containment structure for an insert such as a decorative panel and/or a removable tray that may have a design printed thereon. The table and tray combination can be stacked in nested relationship with like tray and table combinations.

20 Claims, 9 Drawing Sheets

STACKABLE TABLE, TABLE ASSEMBLY, AND TRAY AND TABLE COMBINATION

The invention herein described relates generally to tables and, more particularly, to multi-purpose, multi-function, stackable tray and table combinations that afford benefits and advantages over known table constructions. More specifically, the invention relates to the provision of molded plastic tables and accessories that are aesthetically pleasing in appearance and multi-functional, notwithstanding their being inexpensive to manufacture and easy to handle and easy to transport in a nested stacked arrangement.

BACKGROUND

Many different types of tables have been devised over the years for many different reasons and many of these tables have been molded from plastic. By way of example, a well known inexpensive type of molded plastic table comprises a molded plastic table top that has formed in the bottom thereof sockets for removably receiving a like number of molded plastic legs. This table top has a hollow bottom compartment in which the legs can be stowed for compact storage and/or handling of the table. Often the top has ornamentation thereon to provide a desired effect. Such type of table has found application both indoors and outdoors.

Also known are tables of a unitary molded plastic construction which are capable of being stacked one atop the other. These tables are usually marketed for outside use on a deck, patio, etc.

SUMMARY OF THE INVENTION

The present invention provides a novel table that is useful alone and in combination with a tray and/or other inserts supported atop the table. The table preferably is of a unitary molded plastic construction and is configured for nested stacking with like tables for convenient and compact storage and handling.

According to one aspect of the invention, a table for nested stacking with like tables comprises a table top having a top surface of generally polygonal shape with at least three truncated corners, and a plurality of legs depending from the table top at respective ones of the truncated corners. The top surface has a peripheral edge with at least three corner edge portions and at least three side edge portions extending between the corner edge portions, and the legs, going from top to bottom, diverge outwardly with each being in the form of a channel that opens inwardly for nested receipt of a corresponding leg of a subjacent table of like construction.

In a preferred embodiment, the table top has a square or rectangular shape with four truncated corners. The legs, preferably four in number, each diverge outwardly in a vertical plane bisecting the angle formed between the side edge portions at the corresponding corner. The table top has outer side surfaces, and the legs have outer side surfaces coplanar with the outer side surfaces of the table top at respective sides of the table top. More particularly, the table top has a top wall and a skirt wall depending from the top wall. The skirt wall includes corner portions at the truncated corners and stringer portions extending between the corner portions. The corner portions are sloped relative to adjacent ends of the stringer portions. Preferably, the legs have side walls and a connecting side wall extending between the side walls, and the side walls are coplanar with the stringer portions of the skirt wall at respective sides of the table top. The table top also preferably has an upstanding marginal rim extending along the peripheral edge of the top surface, and the marginal rim includes side edge portions coinciding with a top edge of the stringer portions of the skirt wall and corner edge portions coinciding with a top edge of the corner portions of skirt wall. The marginal rim functions to prevent objects from rolling or sliding off the top surface. The marginal rim also defines a shallow socket for receiving an insert such as a decorative panel and/or a removable tray.

According to another aspect of the invention, a table for nested stacking with like tables, comprises a table top having a top surface of generally polygonal shape with at least three and preferably four corners, and a plurality of legs depending from the table top at respective ones of the corners. The legs, which diverge outwardly going from top to bottom, each are in the form of a three sided channel that opens inwardly for nested receipt of a corresponding leg of a subjacent table of like construction.

In a preferred embodiment, each leg has side walls interconnected by a connecting wall. The table top has outer side surfaces, and the side walls of the legs have outer side surfaces coplanar with the outer side surfaces of the table top at respective sides of the table top. Preferably, the table top has a top wall and reinforcing ribs contiguous with a bottom side of the top wall. The reinforcing ribs include ribs extending from the middle of the table top to respective corners, and the reinforcing ribs have bifurcated end portions extending from a point of joinder to respective corner edges formed by the intersection of the connecting wall with the side walls. The bifurcated end portions have bottom surfaces for engaging a subjacent table of like construction for spacing the top wall of said table above the top wall of the subjacent table.

According to a further aspect of the invention, a table assembly for nested stacking with like tables, comprises a table top and a plurality of legs depending from the table top. The legs are configured and laterally spaced apart sufficiently to clear the table top of a subjacent table of like construction to allow the tables to be stacked in nested relationship. The table assembly also comprises an insert supported atop the table top, and the table top has containment structure integral therewith that laterally interferes with the insert when supported thereon in a predetermined positional relationship to prevent lateral shifting movement of the insert relative to the table top while permitting vertical removal of the insert from the table top.

In a preferred embodiment, the containment structure includes an upstanding rim extending along the perimeter of the table. The insert may be a tray having a bottom wall bounded by an marginal rim wall projecting above the bottom wall and configured to engage and nest within the upstanding rim of the table top. The tray has a lip extending laterally outwardly from a top edge of the marginal rim and resting atop a top edge of the marginal rim, and the lip has opposed handle portions which project laterally outwardly beyond the marginal rim such that it can be engaged from underneath for lifting the tray from the table. In addition, the table includes support structure beneath a top wall of the table top, the support structure including a peripheral skirt and having a bottom abutment for engaging the top of a subjacent table of like construction, the abutment being vertically positioned to provide a vertical gap between the bottom of the skirt and the top of the subjacent table.

According to still another aspect of the invention, there is provided a table and tray combination for nested stacking with like table and tray combinations. The tray includes a bottom wall bounded by an upright marginal wall, and opposed handles extending laterally outwardly from the marginal wall at opposite sides of the tray. The table includes a table top on which the tray is supported and a plurality of legs depending from the table top, the legs being configured and laterally spaced apart sufficiently to clear the tray and table top of a subjacent table and tray combination of identical construction to allow the tray and table combinations to be stacked in nested relationship. The handles have undersides spaced from the table top to permit engagement therebeneath for lifting of the tray from the table top. The table top has containment structure, such as the aforesaid, that laterally interferes with the tray when supported thereon in a predetermined positional relationship to prevent lateral shifting movement of the tray relative to the table top while permitting vertical removal of the tray from the table top.

The foregoing and other features of the invention are hereinafter fully described and particularly pointed out in the claims, the following description and the annexed drawings setting forth in detail certain illustrative embodiments of the invention, these being indicative, however, of but a few of the various ways in which the principles of the invention may be employed.

DETAILED DESCRIPTION

The invention will now be described with respect to preferred embodiments. However, it will be appreciated that other embodiments of the invention may embody one or more of the hereinafter described features of the invention, or modifications thereof. That is, one or more of the herein described features of the invention may be combined to provide a table, table assembly or table and tray combination according to the present invention, and this specification is intended to encompass such permutations of the features of the invention.

Figure 1:
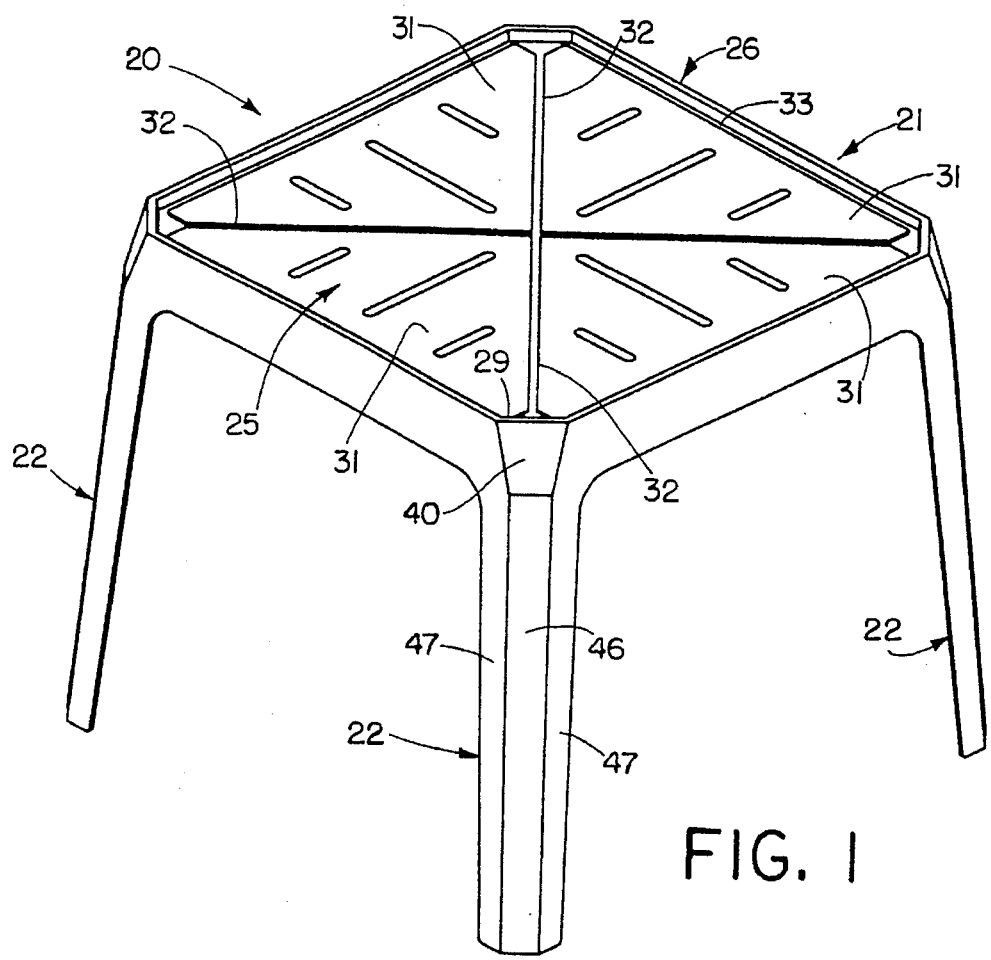
FIG. 1 is a perspective view of a table according to a preferred embodiment of the invention.

Referring now in detail to the drawings and initially to FIG. 1, a preferred embodiment of a table according to the invention is indicated generally at 20. The table generally comprises a table top 21 and a plurality of legs 22 which depend from the table top. In the illustrated preferred embodiment, the table top has a square shape in top plan view with truncated corners at which a respective leg is located. The truncated corners contribute to lateral load strength and stability. However, the table top may be differently shaped (circular, oval, etc.) although usually the table top will have a generally polygonal shape in top plan view with the legs located at respective corners, but not necessarily at every corner, formed between the sides of the polygon. Preferably the sides of the polygon are substantially straight as shown, and the table top may have three or more sides and three or more legs, as may be desired.

The illustrated table construction is molded from plastic as a single piece, as is preferred. This ability to mold the table as a single piece or unitary construction avoids a common prior art practice of assembling separate legs to a table top, which practice is comparatively labor intensive and thus comparatively costly. Often because of cost considerations, the table manufacturer sells the table unassembled and leaves it to the consumer to assemble the table. This aspect of the present invention eliminates this leg assembly drawback associated with prior art table designs that require leg assembly.

Figure 2:
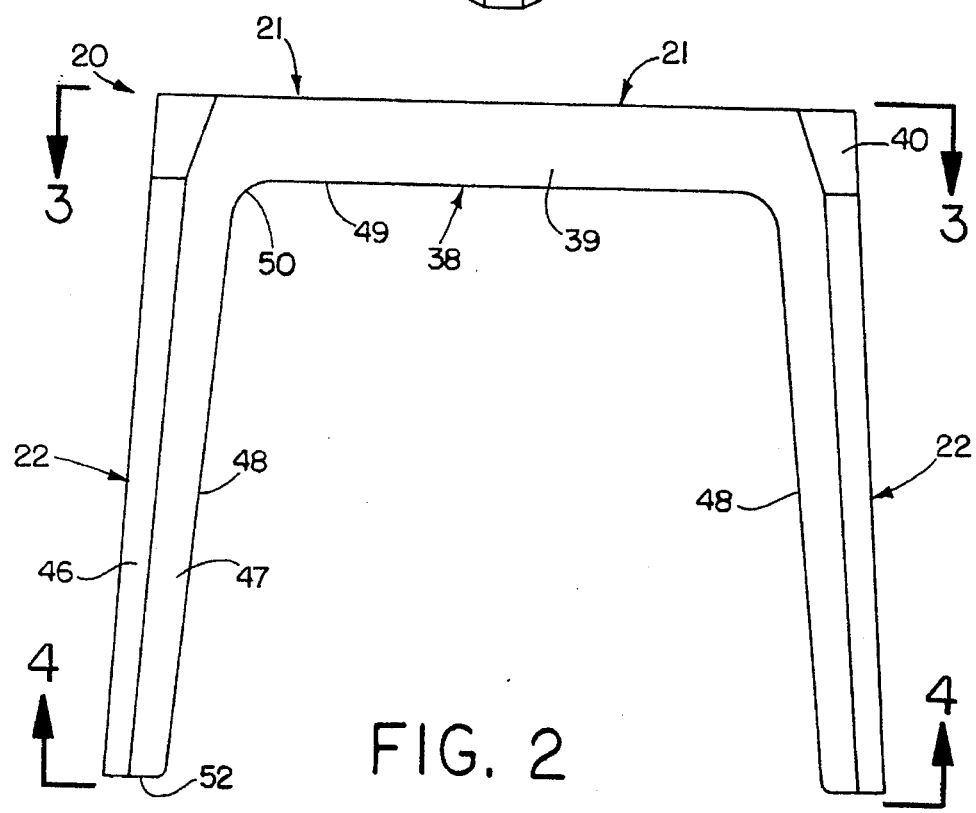
FIG. 2 is a side elevational view of the table of FIG. 1.
Figure 3:
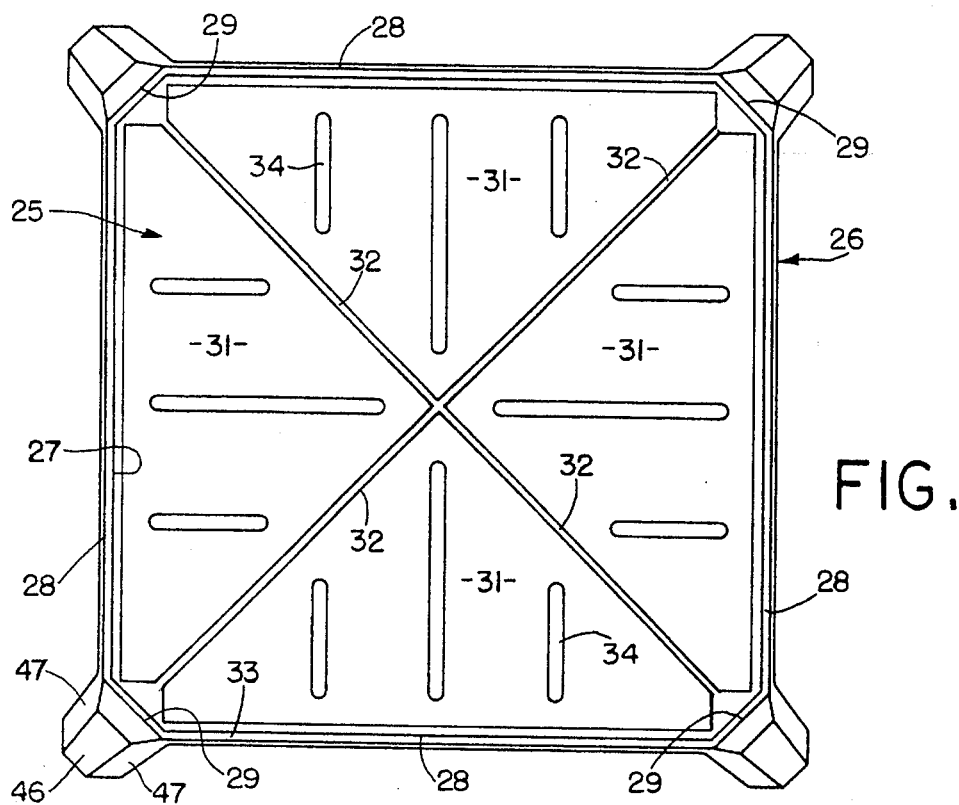
FIG. 3 is a top plan view of the table of FIG. 1 taken from the line 3—3 of FIG. 2.

Referring now additionally to FIGS. 2 and 3, the table top 21 has a top surface 25 that is bounded by a marginal rim 26 that extends along the peripheral edge of the top surface. The marginal rim 26 forms with the top surface a shallow socket 27 for receiving accessories in the form of inserts which are hereinafter described. In the absence of these inserts, the marginal rim provides not only a decorative feature, but it also functions as a containment device or structure to prevent objects from rolling or sliding off the top surface of the table top. For at least this reason, the marginal rim preferably is continuous along the perimeter of the top surface 25. However, the marginal rim may be discontinuous while still serving one or more of the functions herein attributed to the marginal rim.

The marginal rim 26 has long side portions 28 and short corner portions 29. The long side portions 28 correspond to the sides of the polygonal (square) table top whereas the short side portions 29 correspond to truncated corners of the polygonal (square) table top. Preferably, the long side portions 28 are of equal length to provide a regular polygon shape to the top surface such as the illustrated square. Likewise, the short side portions are of equal length so that the top surface has an aesthetically pleasing symmetrical shape, such as that shown. In the illustrated preferred embodiment, the marginal rim has a height above the top surface of about 0.250–0.375 inches (0.635–0.953 cm), whereas the long side portions are about 14 inches (36 cm) in length and the short side portions are about 2 inches (5 cm) in length. Of course, the dimensions may be varied to provide different sizes and shapes of tables for a variety of applications.

As best seen in FIGS. 1 and 3, the top surface 25 of the table top 21 has four triangular land portions 31 that have adjacent sides thereof spaced apart by shallow grooves 32. The grooves 32 extend diagonally and intersect at the center of the top surface. The land portions also have their outer sides spaced from corresponding sides of the marginal rim by a shallow marginal groove 33 that interconnects with the outer ends of the diagonal grooves 32 at the corners of the top surface. Each land portion has associated therewith one or more openings 34, preferably in the form of slots as shown, which extend through the table top. The slots 34 in the illustrated embodiment are multi-functional in that they provide for drainage of liquids such as rain water from the top of the table and for an aesthetically pleasing design pattern in the top surface of the table top. Although not shown, the grooves 32 and 33 may have openings such as holes or slots in the bottoms thereof that extend vertically through the table top to drain liquids that may become captured therein. To facilitate drainage, the drain openings in the top surface may be strategically located at low points of the top surface which may be contoured to cause liquid to flow to the drain openings.

Referring now to FIGS. 2–5, the table top 21 in its preferred form has a relatively thin, planar top wall 36, the top surface of which forms the top surface 25 of the table top. The top wall 36 is bounded by the marginal rim 26. Depending from and forming a continuation of the laterally outer side of the marginal rim is a skirt 38 of approximately the same wall thickness as the top wall. The skirt 38 includes stringer portions 39 which extend between relatively adjacent legs 22 and provide reinforcement and support for the side edges of the top wall 36 intermediate the legs. The skirt also has corner portions 40 between the ends of the stringer portions.

Figure 4:
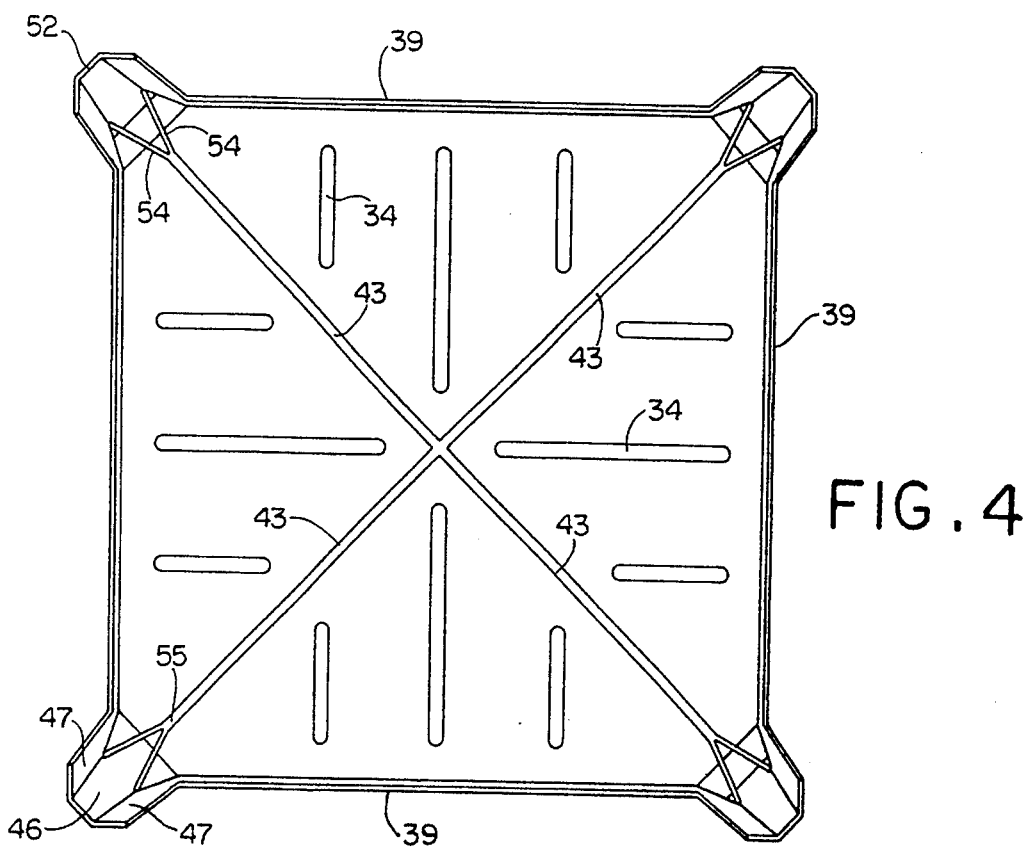
FIG. 4 is a bottom view of the table of FIG. 1 taken from the line 4—4 of FIG. 2.

The top wall 36 is further supported and strengthened by underlying reinforcing ribs 43. Preferably, the reinforcing ribs extend from respective corners of the top wall to the center of the top wall where they meet as shown in FIG. 4. Consequently, in the illustrated embodiment, the ribs are coextensive with the diagonal grooves of the top surface. This is desirable as it serves to hide in the region of the diagonal grooves 32 any shrinkage lines that may form because of the increased part thickness at the reinforcing ribs. As is well known in the plastic molding art, thicker regions may shrink more than relatively adjacent thinner regions and as a result leave depressions coinciding with the thicker regions. These depressions in the illustrated top surface will be aligned with the diagonal grooves 32 thereby becoming part of the groove.

At the corners of the top wall 36, the skirt 38 functions to join the legs 22 to the top wall. The legs 22 are generally in the form of U-shape channels that open inwardly towards the center of the table. As is preferred, each leg, going from top to bottom, diverges laterally outwardly from the respective corner in a vertical plane bisecting the angle formed between the adjacent sides of the polygonal shape top surface. In the case of a square top surface as shown, the legs diverge outwardly in a diagonal direction at the corresponding corners of the table top. As will be further discussed below, the legs are located laterally outwardly of the table top to permit nested stacking of like tables one atop the other.

As best seen in FIGS. 1–4, each leg 22 has a connecting wall 46 extending between the outer edges of a pair of side walls 47. In the illustrated preferred embodiment, the outer surfaces of the side walls 47 of each leg are coplanar with the outer surfaces of the adjacent stringer portions 39 of the table skirt 38. More particularly, the side walls of each leg, which preferably are of about the same thickness as the stringer portions of the skirt, are coplanar with the relatively adjacent stringer portions, as is desired for maximizing top load strength. Also, as best seen in FIG. 2, the inner edges 48 of the side walls of each leg gradually curve and blend into the bottom edges 49 of the adjacent stringer portions of the skirt to form rounded corners 50 for a pleasing appearance and further to avoid stress concentrations at the intersections of the legs and skirt. As is preferred, the plane of the outer surfaces of each stringer portion and the adjacent side walls of the legs is slightly canted from vertical and forms with the plane of the top surface an angle greater than 90 degrees. In the illustrated embodiment, the angle formed is about 95 degrees. In the illustrated embodiment, the legs have a length of about 14 inches (36 cm) and the skirt has a height of about 2 inches (5 cm).

The connecting wall 46 of each leg 22 may be approximately the same thickness as the side walls 47 and the corner portions 40 of the skirt 38. As best seen in FIG. 1, each corner portion 40 has a trapezoidal shape and provides at its outer side a sloped transition surface between the top edge of the connecting wall 46 of the corresponding leg 22 and the corner portion 29 of the marginal rim. As is preferred, the connecting wall 46 is slightly canted to vertical and forms with the plane of the top surface an angle greater than 90 degrees. In the illustrated embodiment, this angle is about 95 degrees, and the angle formed between each corner portion of the skirt 38 and the top surface 25 is about 110 degrees. The sloped corner portions 40 contribute to the lateral load strength and stability of the table.

At the bottom of each leg 22 the connecting and side walls 46 and 47 thereof terminate at bottom edge surfaces that are coplanar and parallel to the plane of the top surface. As result of this and the foregoing construction of the legs, the legs have a U-shape footprint with the U opening inwardly as shown in FIG. 4. This three edge or sided foot 52 of each leg provides for stable engagement with floor surfaces of various types. The three sided foot will bite into carpet, sand or other at least partially penetrable surfaces to cooperate therewith to prevent shifting or rotation of the table. The three edge foot also provides for stable support on hard unpenetrable surfaces.

Figure 5:
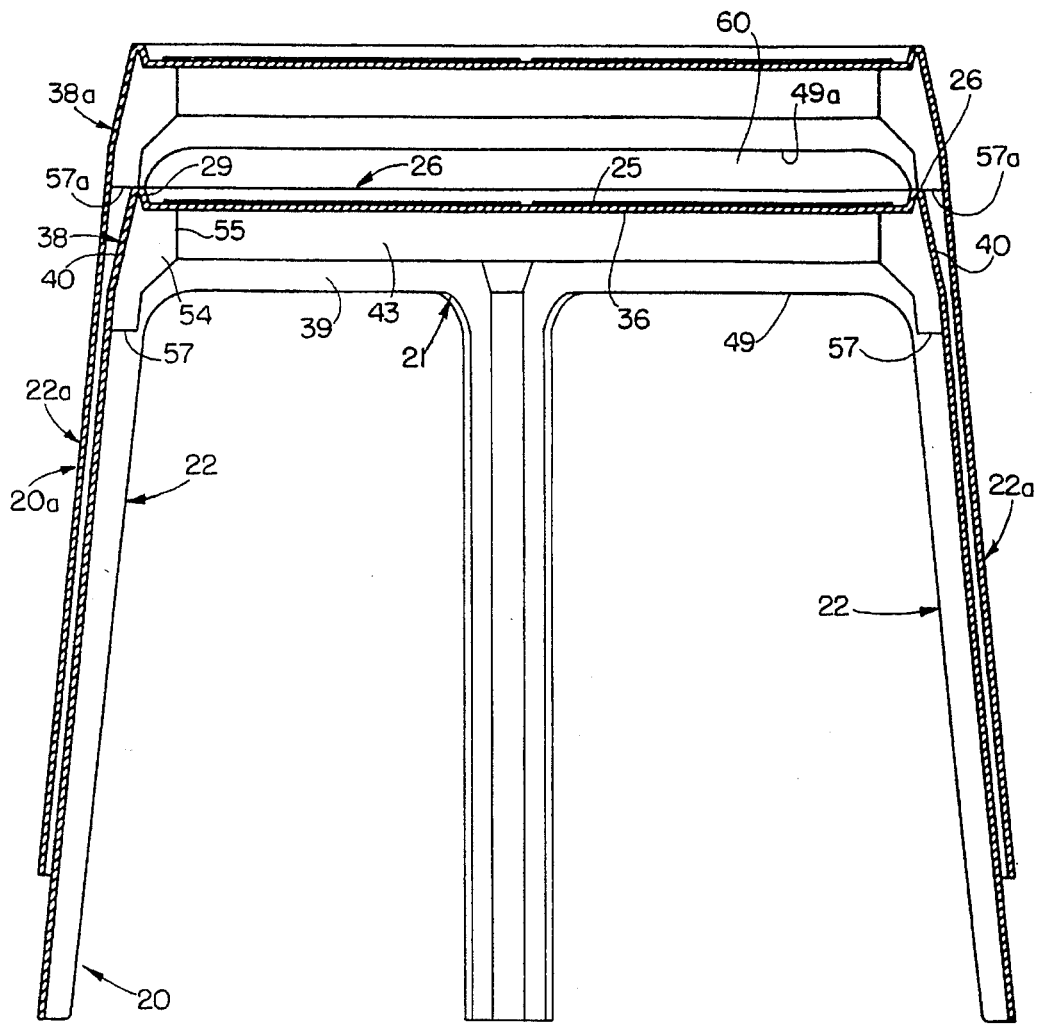
FIG. 5 is a diagonal cross-sectional view of the table of FIG. 1 taken substantially along the line 5—5 of FIG. 3, the table being shown stacked with another like table.

As shown in FIGS. 4 and 5, the reinforcing ribs 43 have bifurcated outer end portions 54 that extend from a point 55 of joinder outwardly and downwardly to form gussets that extend to and join with the connecting wall 46 of the corresponding leg 22 at the edges thereof, thereby to provide added rigidifying support at the upper end of the leg. These outer end portions 54 also function as abutments or spacers having coplanar abutment surfaces 57 for resting atop a subjacent table when the tables are stacked one atop the other. The elevation of these coplanar bottom surfaces relative to the top surface 25 is selected to provide a desired vertical positional relationship between the bottom edges 49 of the stringer portions 39 of the skirt 38 and the top of a subjacent table in a nested stack of tables.

In FIG. 5, a second table 20a is shown stacked atop the table 20. The table 20a is identical to the table 20 and like parts are designated by like reference numerals except that the suffix "a" is used in conjunction with the table 20a to distinguish between like parts of the tables 20 and 20a.

As shown, the bottom abutment surfaces 57 of the outer end portions 54 of the reinforcing ribs 43 horizontally overlap the corner portions of the marginal rim 26. Consequently, the bottom abutment surfaces 57a of table 20a will overlay and rest atop the marginal rim 26 of the subjacent table 20 at the corners thereof. In like manner additional tables may be stacked atop the tables 20 and 20a.

The vertical positional relationship provided between the tops of the tables 20 and 20a is such that the legs 22 nest within the legs 22a at corresponding corners with no or minimal interference, i.e., with a loose fit. Preferably, the legs 22 and 22a of the tables 20 and 20a are prevented from becoming wedged together as this makes separation of the tables difficult. The vertical positional relationship also preferably provides, as indicated at 60, a space between the bottom edge 49a of the skirt 38a and the top of the subjacent table 20 intermediate the legs 22a, as is desired to accommodate the handles of a tray accessory that will now be described.

Figure 6:
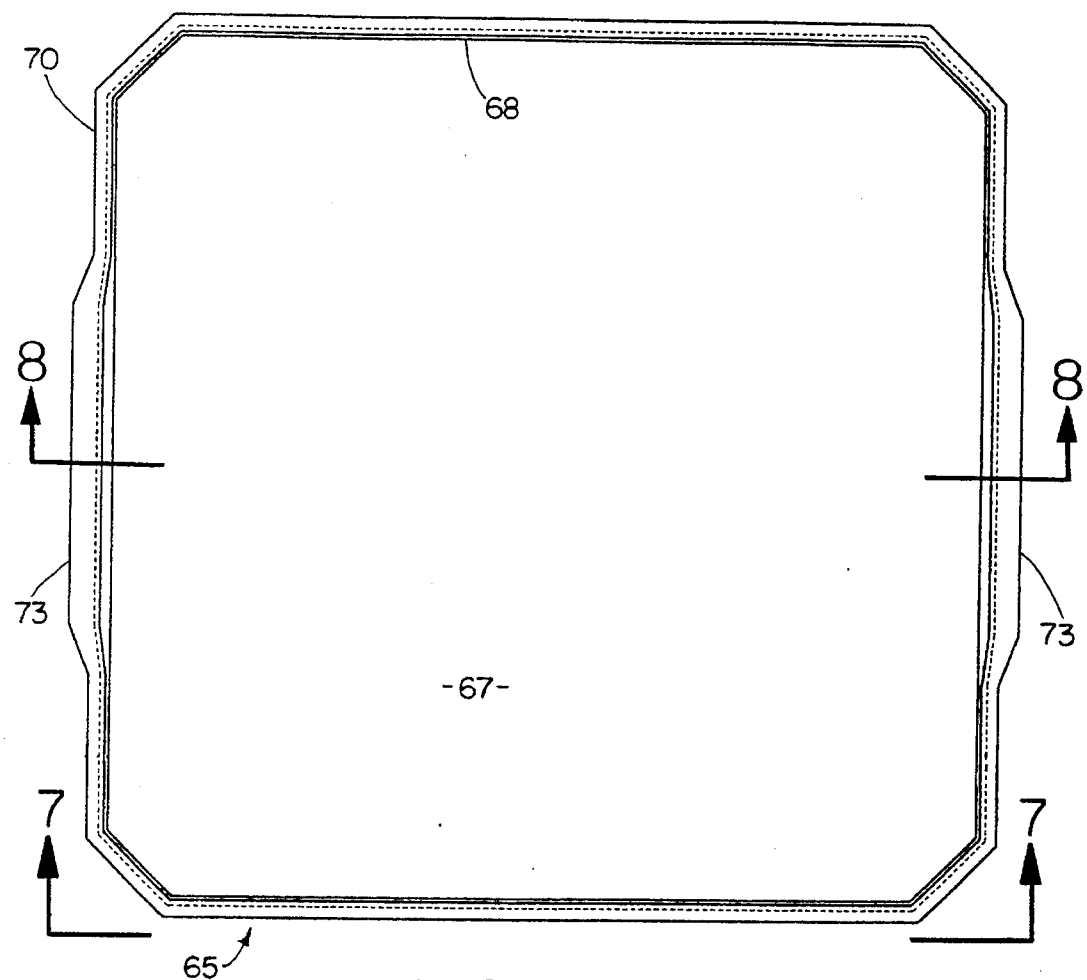
FIG. 6 is a top plan view of a tray according to a preferred embodiment of the invention.
Figure 7:
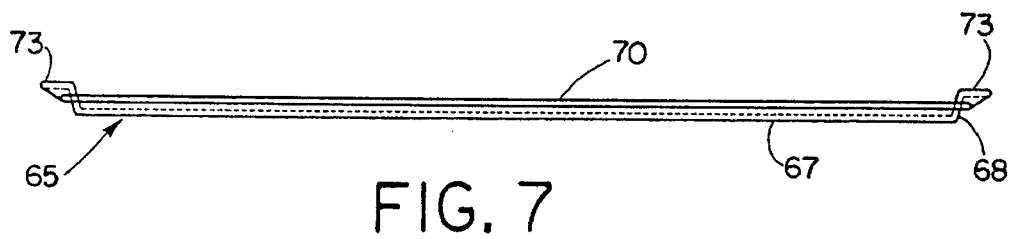
FIG. 7 is a side elevational view of the tray of FIG. 6 taken from the line 7—7 of FIG. 6.
Figure 8:
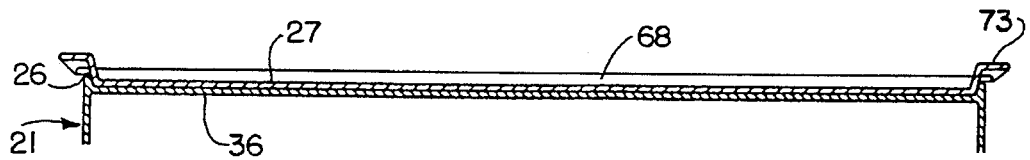
FIG. 8 is a fragmentary cross-sectional view of the tray of FIG. 6 in combination with the table of FIG. 1.
Figure 9:
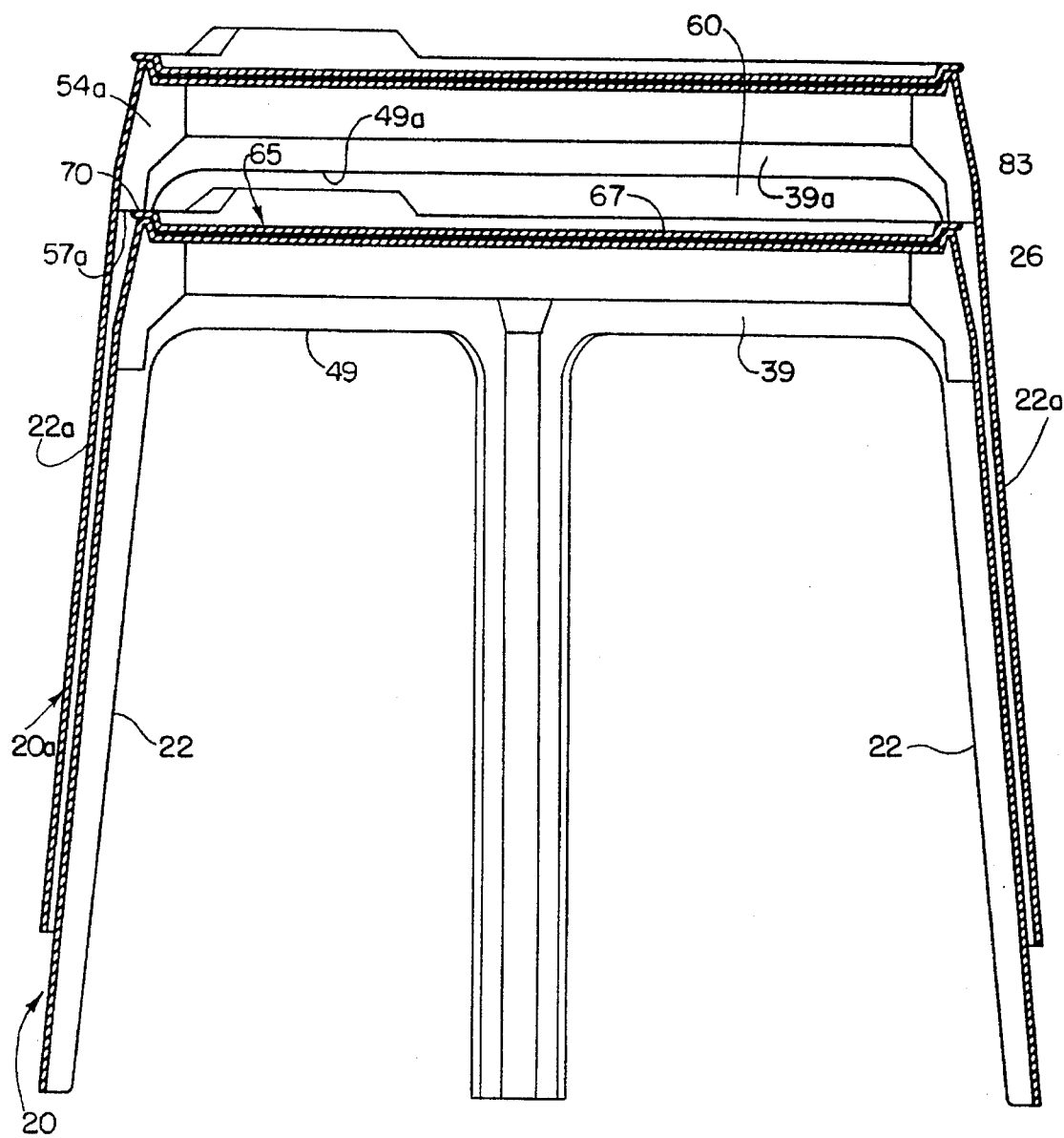
FIG. 9 is a diagonal cross-sectional view of the tray and table of FIG. 8 shown stacked with a like tray and table combination.

In FIGS. 6–8, there is illustrated a tray 65 that can be used in combination with the table 20 to provide a novel tray and table combination according to the invention. The tray 65 has a bottom wall 67 bounded by a marginal rim wall 68 projecting above the bottom wall and configured to engage and nest within the upstanding rim 26 of the table top 21 of the table 20. In the illustrated preferred embodiment, the bottom wall 67 is generally square in plan view with the corners of the square being truncated. More generally, the tray is configured to be received with a close fit within the shallow socket 27 of the table top 21 with the marginal rim wall thereof engaging the marginal rim of the table top as seen in FIGS. 8 and 9. The marginal rim wall 68 forming the peripheral edge of the tray coacts with the marginal rim 26 of the table top to prevent lateral and rotational movement of the tray relative to the table top. In this context the marginal rim functions as preferred containment structure for preventing such lateral and rotational movement of the tray while permitting vertical removal of the tray.

The tray 65 also has a peripheral lip 70 extending laterally outwardly from the top edge of the marginal rim wall 68. For the most part, the lip 70 extends beyond the marginal rim wall by an amount just sufficient to overlie the marginal rim 26 of the table 20. Also, the height of the lip relative to the bottom wall 67 of the tray is such that the lip will rest atop the marginal rim 26 of the table when the tray is set in the shallow socket 27 defined by the marginal rim with its bottom wall 67 resting atop the top surface 25 of the table top 21 as seen in FIGS. 8 and 9. Preferably, the peripheral lip 70 has at opposite sides of the tray two oppositely directed wider and relatively elevated portions that form handles 73 to facilitate lifting of the tray from the table. When the tray is set atop the table, the handles will be spaced above and laterally outwardly of the marginal rim 26 of the table top to allow a person's fingers to fit therebeneath and engage the underside of the handles for easy and convenient lifting of the tray or setting of the tray atop the table.

Figure 10:
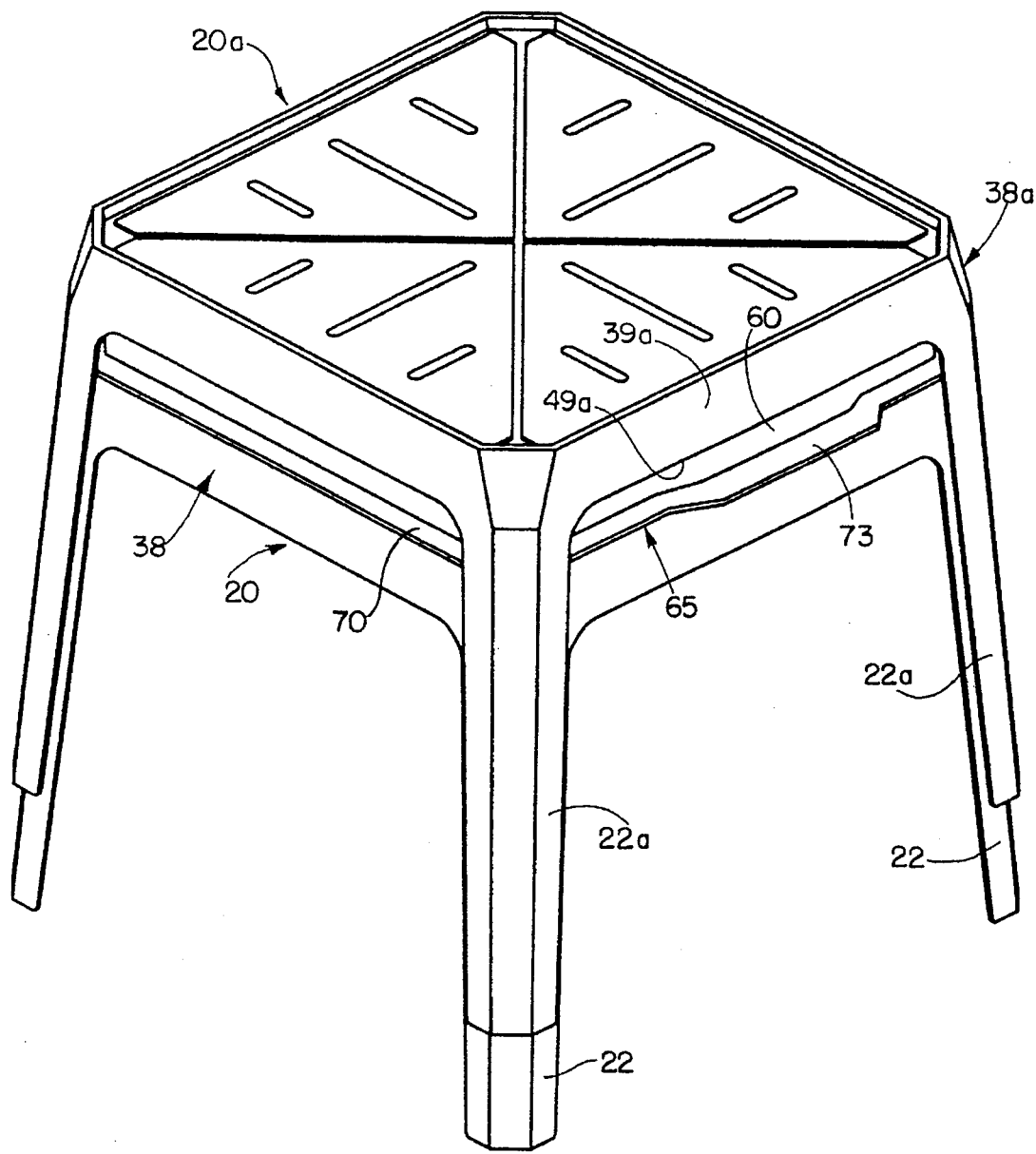
FIG. 10 is a perspective view showing the stacked tray and table combinations of FIG. 9 with the top tray removed.
Figure 11:
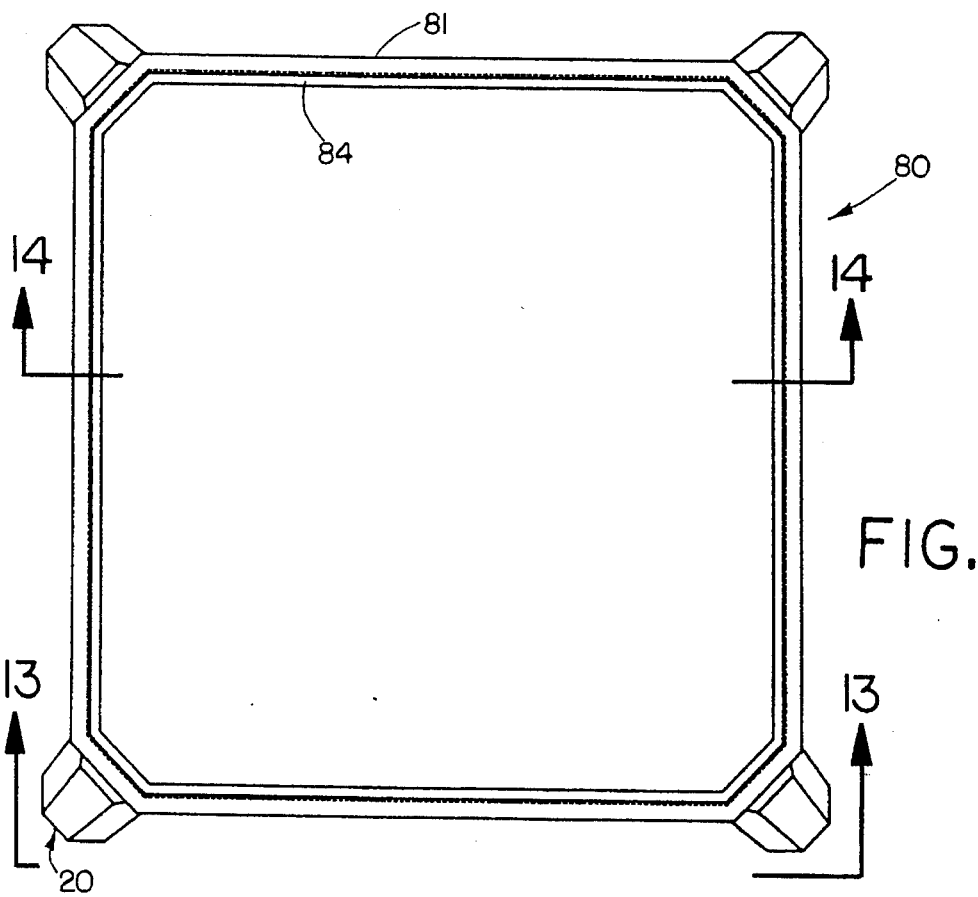
FIG. 11 is a top plan view of another embodiment of tray in combination with the table of FIG. 1.
Figure 12:
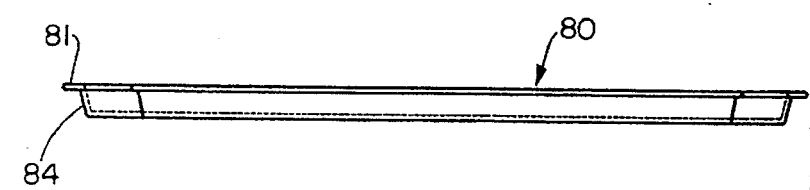
FIG. 12 is a side elevational view of the tray of FIG. 11.
Figure 13:
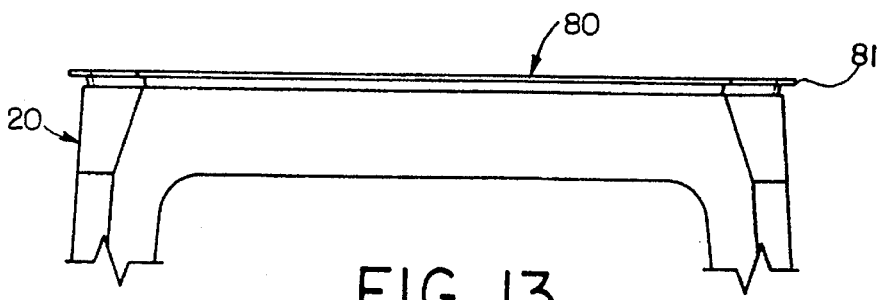
FIG. 13 is a fragmentary side elevational view of the tray and table combination of FIG. 11 taken from the line 13—13 of FIG. 11.
Figure 14:
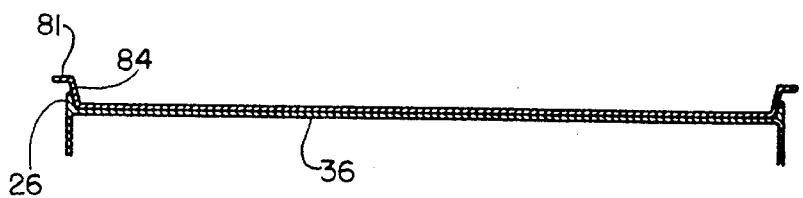
FIG. 14 is a fragmentary cross-sectional view of the tray and table combination of FIG. 11 taken along the line 14—14 of FIG. 11.

The handles 73 are preferably centered with respect to corresponding sides of the tray 65 and have a length less than the lengths of the corresponding tray sides and, more particularly, less than the length of the spacing between the legs 22 at the elevation of the bottom surfaces 49 of the stringers 39 as seen in FIG. 10. This is necessary to avoid interference with the legs of a superjacent table 20a as illustrated in FIG. 10. Also, the handles are accommodated in the vertical space 60 between the bottom edge 49a of the skirt 38a of the superjacent table 20a and the top of the marginal rim 26 of the subjacent table 20. As also seen in FIG. 9, the outer end portions 54a of the reinforcing ribs of the superjacent table, which function as spacers, will rest atop the peripheral lip 70 of the tray 65 of the subjacent table 20 at the corners of the table. This will increase the stacking height of the nested tables by only the collective thickness of the peripheral lips of the trays included in the stack.

Referring now to FIGS. 11–14, a modified tray 80 may be provided in combination with the table 20. The tray 80 is the same as the tray except the peripheral lip 81 is the same as the handle 73 of the tray 65 of FIGS. 6–10 along the entire perimeter of the tray. Accordingly, the peripheral lip 81 may be engaged at its underside by a user's fingers anywhere along the perimeter of the tray for easy and convenient lifting. However, for stacking of the tables with the tray 80 in place, the peripheral lip must not project beyond the marginal rim 26 by an amount that would interfere with the legs 22 or skirt 38 of a superjacent table in a stack thereof. As best seen in FIG. 9, there is sufficient clearance with the upper portion of the legs at the corners of the table for the peripheral lip of a tray to project outwardly beyond the marginal lip of the table top, this clearance being indicated at 83.

Because of the peripheral lip 81 of the tray 80 is relatively elevated at the corners when compared to the peripheral lip 70 of the tray 65 of FIGS. 6–10, the stacking height of a stack of such table and tray combinations will be correspondingly higher. Notwithstanding, the table and tray combinations will still substantially nest within one another even when the trays are in place. That is, there still is no need to remove the trays in order to stack the tables. As a further consequence of this higher elevation, the peripheral lip 81 will not rest atop the marginal rim 26. Therefore, to obtain the same stacking height capability as the trays and tables of FIGS. 6–10, the wall thickness of the marginal wall 84 and peripheral lip 81 of the tray may be increased to handle the higher load that will be borne thereby when compared to the trays and tables of FIGS. 6–10.

Figure 15:
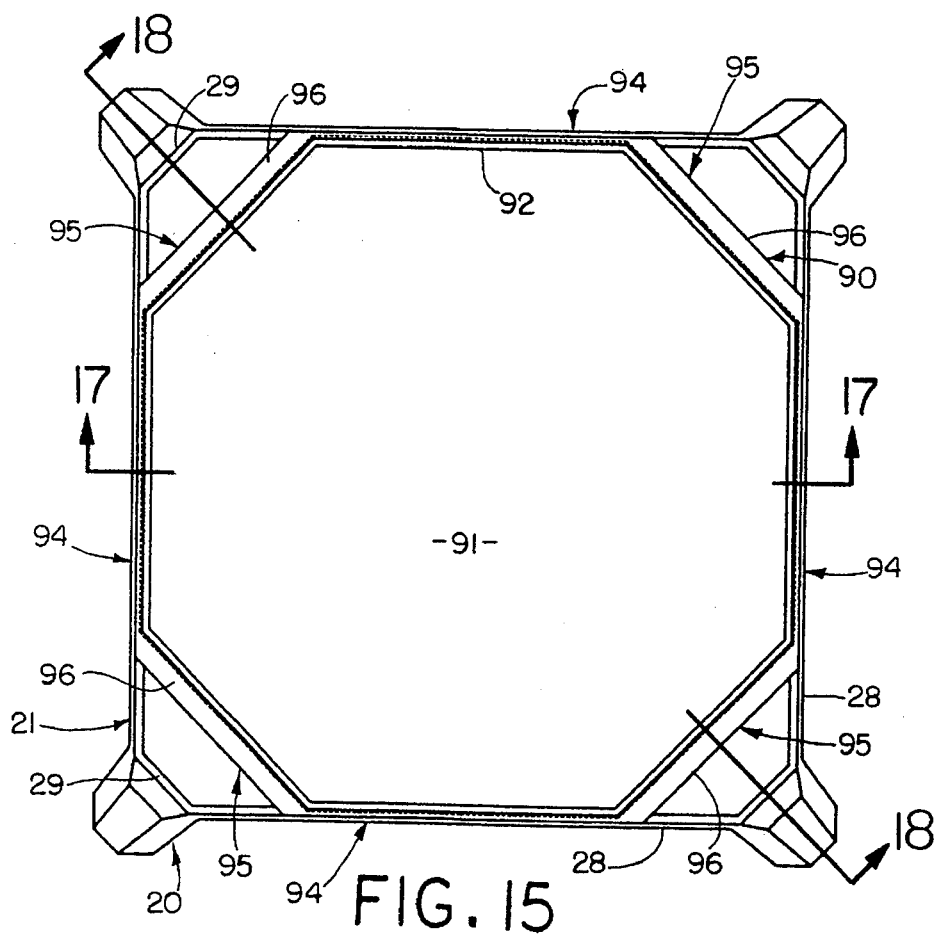
FIG. 15 is a top plan view of a further embodiment of tray in combination with the table of FIG. 1.
Figure 16:
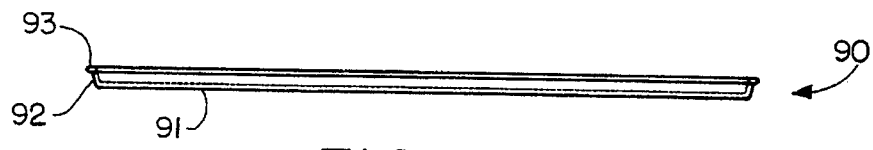
FIG. 16 is a side elevational view of the tray of FIG. 15.
Figure 17:
FIG. 17 is a fragmentary cross-sectional view of the tray and table combination of FIG. 15 taken along the line 17—17 thereof.
Figure 18:
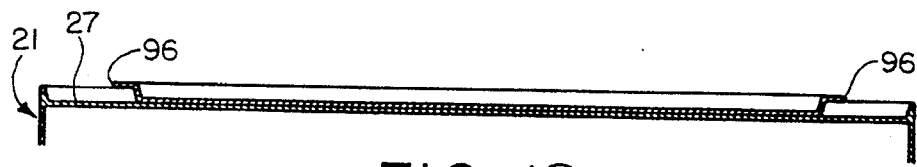
FIG. 18 is a fragmentary diagonal cross-sectional view of the tray and table combination of FIG. 15 taken along the line 18—18 thereof.
Figure 19:
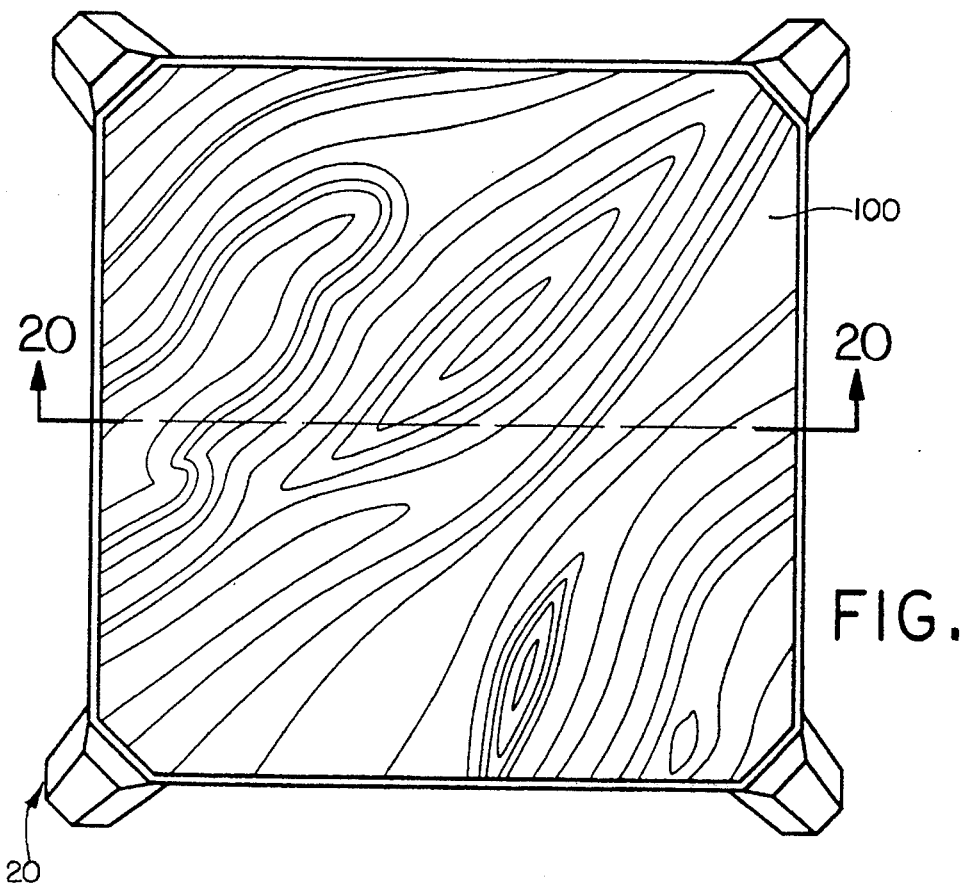
FIG. 19 is a top plan view of the table of FIG. 1 in combination with another form of insert.

The present invention also embodies trays of different shapes. By way of example, FIGS. 15–18 show a tray 90 that is octagonal in plan view and hence a tray that has more sides than the table top 21. As shown, the tray 90 has an octagonal bottom wall 91, a marginal wall 92 and a peripheral lip 93. The tray is dimensioned for close fitting receipt in the shallow socket 27 of the table 20 with four sides indicated at 94 of the tray's marginal wall 92 engaging respective side portions 28 of the marginal rim 26 of the table top of the table and the other four sides indicated at 95 being uniformly spaced inwardly from the corner portions 29 of the marginal rim of the table top. The peripheral lip 93 extending along these latter four sides 95 projects outwardly beyond the marginal wall 92 of the tray to form four handles 96 arranged as two sets of opposed handles as best seen in FIGS. 15 and 18. The handles 96, i.e., the projecting portions of the peripheral lip 93, will be spaced above the top surface of the table and inwardly of the corner portions 29 of the marginal rim of the table top sufficiently to allow a user's finger to be inserted underneath the handle for lifting of the tray from the table. In the illustrated tray the bottom surface of the peripheral lip 93 is at the same elevation as the top surface of the marginal rim 26 when the tray is set in place. However, it will be appreciated that if desired the peripheral lip may be disposed at a higher elevation relative to the top surface of the table top. That is, the peripheral lip may be spaced above the plane of the bottom surface of the tray by an amount greater than the height of the marginal rim above the top surface of the table top. This can be tolerated because the increased height of the peripheral lip can be accommodated within the space between the table tops when the tables are stacked with the trays in place.

Figure 20:
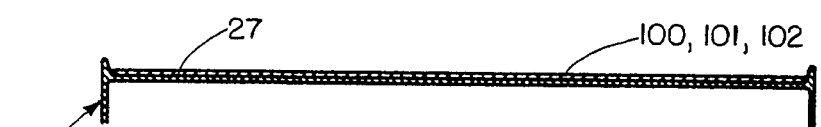
FIG. 20 is a fragmentary cross-sectional view of the table assembly of FIG. 19 taken along the line 20—20 thereof.
Figure 21:
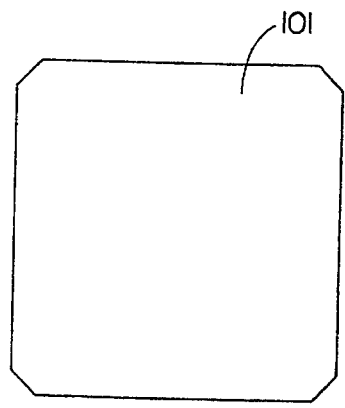
FIGS. 21 and 22 are plan views of still other inserts that may be used in combination with the table of FIG. 1.
Figure 22:
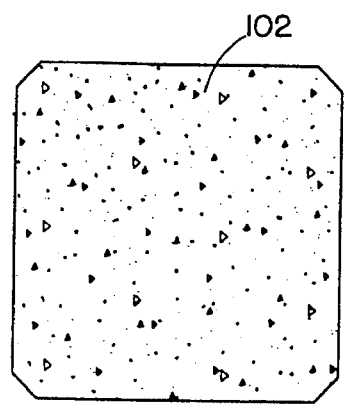

Referring now to FIGS. 19–22, it will be seen different types of inserts other than a tray may be received in the shallow socket 27 of the table 20. Although the inserts may be otherwise shaped, the inserts shown in FIGS. 19–20 correspond to the shape of the top surface of the table top such that they cover the top surface in its entirety. The insert 100 in FIG. 19 has a wood grain appearance on the top surface thereof, the insert 101 in FIG. 21 has a solid flat top surface, and the insert 102 of FIG. 22 has a decorative pattern surface that may be textured, if desired. Each insert is a thin panel having a thickness less than the depth of the shallow socket 27 of the table top as seen in FIG. 20, whereby the marginal rim will project above the top surface of the insert. However, the panel thickness may be varied as desired to provide, for example, a top surface flush with or above the top edge of the marginal rim.

The inserts 100–102 may be inserted in the shallow socket 27 of table 20 with either face thereof facing upwardly and thus be viewable. The insert may be secured in the shallow socket as by use of an adhesive, press fit, fasteners, etc., although preferably the insert is removably placed in the shallow socket so that it can be removed when desired and replaced by another insert or turned over to present its bottom surface to view. Hence, for added versatility, both sides of the inserts may be provided with a desired finish that may be the same or more preferably different.

The inserts may have applied thereto on one or both faces thereof any one of variety of designs, indicia, patterns, etc., whereby the table may be specially adapted for different applications. For example, any of the above inserts, including the trays, may have lithographed on a face thereof a multi-color cartoon character to target the use of the table by a child. As will be appreciated, the table may be used as a desk, drawing table or the like by a very young child who can sit at the table with their legs extending underneath the table. For larger children, the table (dimensioned as herein described) may be used as a night stand, display table or the like. As above indicated, the table size may be varied to increase the number of different applications of the table.

As above indicated, one or more of the herein described features of the invention may be combined in different ways than those specifically shown and/or described herein. By way of example, a tray like the tray shown in FIGS. 6 and 7 may be used in combination with the table having an insert like that shown in FIG. 19. In this combination the tray and insert could be interchangeably set in the shallow socket of the table or both may be set in the shallow socket as would normally be the case, with the insert positioned beneath the tray.

The above described trays and inserts may be made of polypropylene and the table may be made of polypropylene or polyethylene, by way of example. Also, a clear insert may be made of polystyrene.

Although the invention has been shown and described with respect to several preferred embodiments, it will be apparent that equivalent alterations and modifications will occur to others skilled in the art upon the reading and understanding of this specification. The present invention includes all such equivalent alterations and modifications, and is limited only by the scope of the following claims.

What is claimed is:

1. A table and tray combination for nested stacking with like table and tray combinations, said tray including a bottom wall bounded by an upright marginal wall, and opposed handles extending laterally outwardly from said marginal wall at opposite sides of said tray; and said table including a table top on which said tray is supported and a plurality of legs depending from said table top, said legs being configured and laterally spaced apart sufficiently to clear the tray and table top of a subjacent table and tray combination of identical construction to allow the tray and table combinations to be stacked in nested relationship.

2. A table and tray combination as set forth in claim 1, wherein said table top has a top surface of generally polygonal shape with at least three truncated corners, said top surface having a peripheral edge with at least three corner edge portions and at least three side edge portions extending between said corner edge portions, and said legs depend from said table top at respective ones of said truncated corners, said legs, going from top to bottom, diverging outwardly and each being in the form of channel that opens inwardly for nested receipt of a corresponding leg of a subjacent table of like construction.

3. A table and tray combination as set forth in claim 2, wherein said table top and legs are of a unitary molded plastic construction.

4. A table and tray combination as set forth in claim 2, wherein said table top has outer side surfaces, and said legs have outer side surfaces coplanar with said outer side surfaces of said table top at respective sides of said table top.

5. A table and tray combination as set forth in claim 2, wherein said table top has a top wall and a skirt wall depending from said top wall, said skirt wall includes corner portions at said truncated corners and stringer portions extending between said corner portions, and said corner portions are sloped relative to adjacent ends of said stringer portions.

6. A table and tray combination as set forth in claim 5, wherein said legs have side walls and a connecting wall extending between said side walls, and said side walls are coplanar with said stringer portions of said skirt walls at respective sides of said table top.

7. A table and tray combination as set forth in claim 6, wherein said table top has an upstanding marginal rim extending along the peripheral edge of said top surface, and said marginal rim includes side edge portions coinciding with a top edge of said stringer portions of said skirt wall and corner edge portions coinciding with a top edge of said corner portions of skirt wall.

8. A table and tray combination as set forth in claim 2, wherein said legs each diverge outwardly in a vertical plane bisecting an angle formed between the side edge portions at the corresponding corner.

9. A table and tray combination as set forth in claim 1, wherein said table top has a top surface of generally polygonal shape with at least three corners, and said legs depend from said table top at respective ones of said corners, said legs, going from top to bottom, diverging outwardly and each being in the form of a three sided channel that opens inwardly for nested receipt of a corresponding leg of a subjacent table of like construction.

10. A table and tray combination as set forth in claim 9, wherein each said leg has side walls interconnected by a connecting wall.

11. A table and tray combination as set forth in claim 10, wherein said table top has a top wall and reinforcing ribs contiguous with a bottom side of said top wall, said reinforcing ribs include at least one rib extending from the middle of said table top to a respective one of said corners, and said one reinforcing rib has bifurcated end portions extending from a point of joinder to respective corner edges formed by the intersection of the connecting wall and said side walls.

12. A table and tray combination as set forth in claim 11, wherein said bifurcated end portions have bottom surfaces for engaging a subjacent table of like construction for spacing said top wall of said table above the top wall of the subjacent table.

13. A table and try combination as set forth in claim 10, wherein said table top has outer side surfaces, and said side walls of said legs have outer side surfaces coplanar with said outer side surfaces of said table top at respective sides of said table top.

14. A table and tray combination as set forth in claim 1, wherein said table top has containment structure that laterally interferes with said tray when supported thereon in a predetermined positional relationship to prevent lateral shifting movement of said tray relative to said table top while permitting vertical removal of said tray from said table top.

15. A table and tray combination as set forth in claim 14, wherein said containment structure includes an upstanding rim extending along the perimeter of said table.

16. A table and tray combination as set forth in claim 15, wherein said tray has a lip extending laterally outwardly from a top edge of said marginal wall and resting atop a top surface of said upstanding rim.

17. A table and tray combination as set forth in claim 16, wherein said lip has opposed handle portions forming said handles, said handle portions projecting laterally outwardly beyond said marginal rim such that said handle portions can be engaged from underneath for lifting said tray from said table.

18. A table and tray combination as set forth in claim 15, wherein said table includes support structure beneath said table top, said support structure including a peripheral skirt and having a bottom abutment for engaging the top of a subjacent table of like construction, said abutment being vertically positioned to provide a vertical gap between the bottom of the skirt and the top of the subjacent table.

19. A table and tray combination as set forth in claim 1, wherein said table is of a unitary molded plastic construction.

20. A table and tray combination as set forth in claim 1, wherein said handles have undersides spaced from said table top to permit engagement therebeneath for lifting of said tray from said table top.

* * * * *